US012599511B2

(12) United States Patent
Yoon et al.

(10) Patent No.: US 12,599,511 B2
(45) Date of Patent: Apr. 14, 2026

(54) ABSORBENT ARTICLE

(71) Applicant: LG Chem, Ltd., Seoul (KR)

(72) Inventors: Kiyoul Yoon, Daejeon (KR);
Myoungjin Shin, Daejeon (KR);
Seongkyun Kang, Daejeon (KR); Yu Jin Kim, Daejeon (KR); Gicheul Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 341 days.

(21) Appl. No.: 18/266,063

(22) PCT Filed: May 11, 2022

(86) PCT No.: PCT/KR2022/006773
§ 371 (c)(1),
(2) Date: Jun. 8, 2023

(87) PCT Pub. No.: WO2022/240199
PCT Pub. Date: Nov. 17, 2022

(65) Prior Publication Data
US 2024/0091075 A1 Mar. 21, 2024

(30) Foreign Application Priority Data

May 11, 2021 (KR) ........................ 10-2021-0060742
May 11, 2022 (KR) ........................ 10-2022-0057890

(51) Int. Cl.
*A61F 13/494* (2006.01)
*A61F 13/49* (2006.01)
(Continued)

(52) U.S. Cl.
CPC .. *A61F 13/49426* (2013.01); *A61F 13/49017* (2013.01); *A61F 2013/15365* (2013.01);
(Continued)

(58) Field of Classification Search
CPC ...... A61F 13/49017; A61F 2013/15365; A61F 2013/15406; A61F 2013/15463;
(Continued)

(56) References Cited

U.S. PATENT DOCUMENTS 4,861,539 A * 8/1989 Allen ........................ C08F 8/30
264/211.13
2002/0064624 A1 5/2002 Mizutani et al.
(Continued)

FOREIGN PATENT DOCUMENTS

CN 1771015 A 5/2006
CN 107106372 A 8/2017
(Continued)

OTHER PUBLICATIONS

EESR for Application No. 22807846.5 dated Feb. 23, 2024. 6 pgs.
(Continued)

*Primary Examiner* — Susan S Su
(74) *Attorney, Agent, or Firm* — Lerner David LLP

(57) ABSTRACT
Provided is an absorbent article exhibiting an improved effect of preventing the body fluid from leaking by including a superabsorbent polymer film having excellent absorbency in three-dimensional gathers.

6 Claims, 2 Drawing Sheets

100

(51) Int. Cl.
    *A61F 13/15*          (2006.01)
    *A61F 13/53*          (2006.01)

(52) U.S. Cl.
    CPC .............. *A61F 2013/15406* (2013.01); *A61F 2013/15463* (2013.01); *A61F 2013/530481* (2013.01)

(58) Field of Classification Search
    CPC .......... A61F 2013/530481; A61F 13/49; A61F 13/494; A61F 13/53; A61F 13/49426
    See application file for complete search history.

(56) References Cited

U.S. PATENT DOCUMENTS

| | | | |
|---|---|---|---|
| 2006/0206090 A1 | 9/2006 | Mori | |
| 2015/0216734 A1 | 8/2015 | Umemoto | |
| 2017/0348163 A1 | 12/2017 | Lakso et al. | |
| 2020/0384441 A1* | 12/2020 | Yoon .................... | C08F 220/06 |
| 2024/0082819 A1 | 3/2024 | Yoon et al. | |

FOREIGN PATENT DOCUMENTS

| | | | |
|---|---|---|---|
| CN | 111465636 A | 7/2020 | |
| EP | 3708608 A1 | 9/2020 | |
| JP | H05-009525 U | 2/1993 | |
| JP | 2002-159531 A | 6/2002 | |
| JP | 2003-265529 A | 9/2003 | |
| JP | 4326391 B2 | 9/2009 | |
| JP | 2010094322 A | 4/2010 | |
| JP | 2010-111717 A | 5/2010 | |
| JP | 5086036 B2 | 11/2012 | |
| JP | 2016-010515 A | 1/2016 | |
| JP | 5988714 B2 | 9/2016 | |
| JP | 2017-169967 A | 9/2017 | |
| JP | 6269245 B2 | 1/2018 | |
| JP | 2018-130222 A | 8/2018 | |
| JP | 2018140067 A | 9/2018 | |
| JP | 2019024843 A | 2/2019 | |
| JP | 6725544 B2 | 7/2020 | |
| JP | 6813274 B2 | 1/2021 | |
| JP | 2021-504530 A | 2/2021 | |
| KR | 101907369 B1 | 12/2018 | |
| KR | 20190071619 A | 6/2019 | |
| WO | 2017077750 A1 | 5/2017 | |
| WO | 2019022057 A1 | 1/2019 | |
| WO | 2019038867 A1 | 2/2019 | |
| WO | WO-2019117670 A1 * | 6/2019 | ........... C08F 220/26 |

OTHER PUBLICATIONS

Schwalm, R. "UV Coatings Basics, Recent Developments and New Application," Elsevier Science, Dec. 21, 2006, p. 115. (3 pgs.).
Odian, G. "Principles of Polymerization" Dec. 1981, p. 203, Wiley Interscience Publication. (3 pgs.).
International Search Report for Application No. PCT/KR2022/006773 mailed Aug. 29, 2022. 3 pages.

\* cited by examiner

【FIG. 1】
100
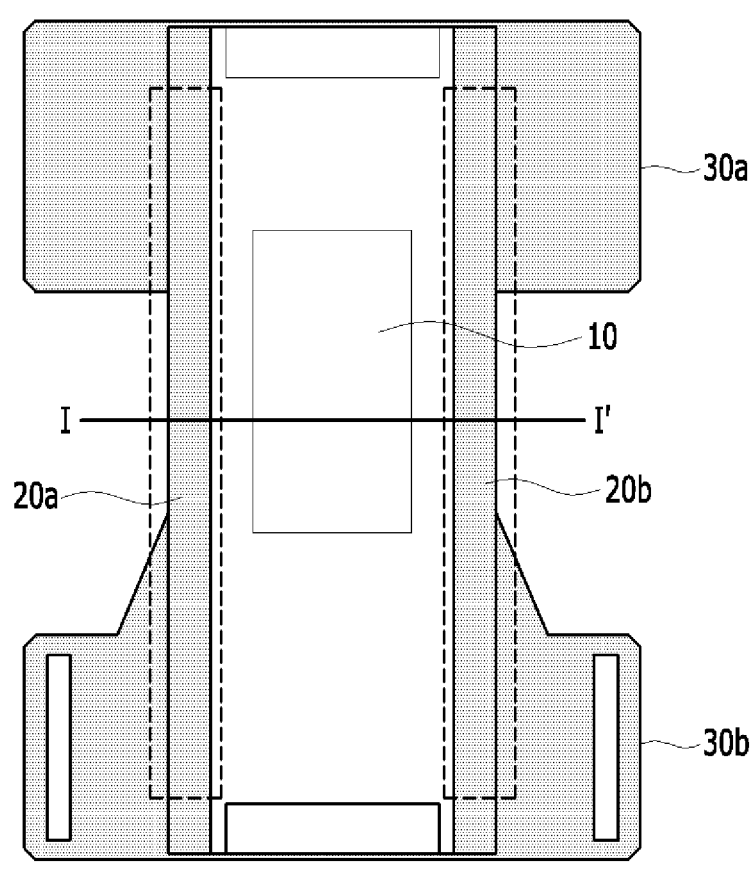

【FIG. 2】
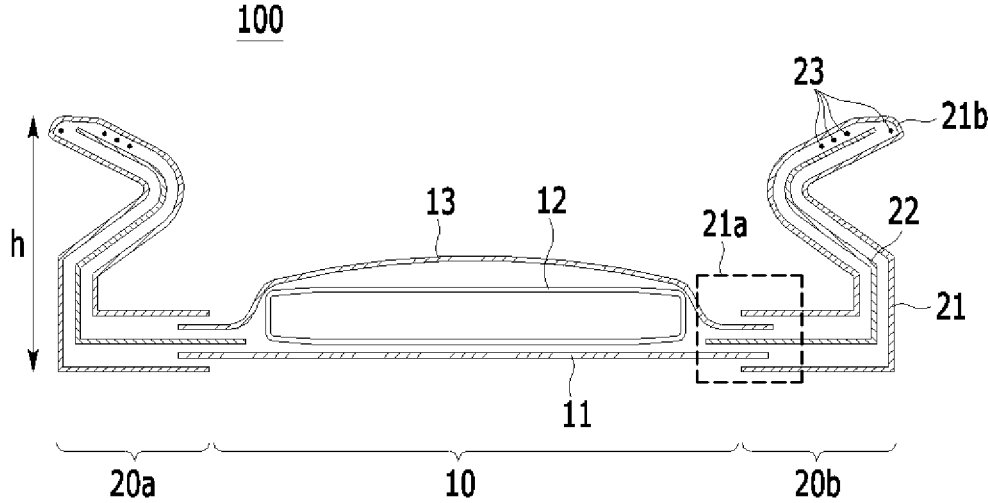
【FIG. 3】
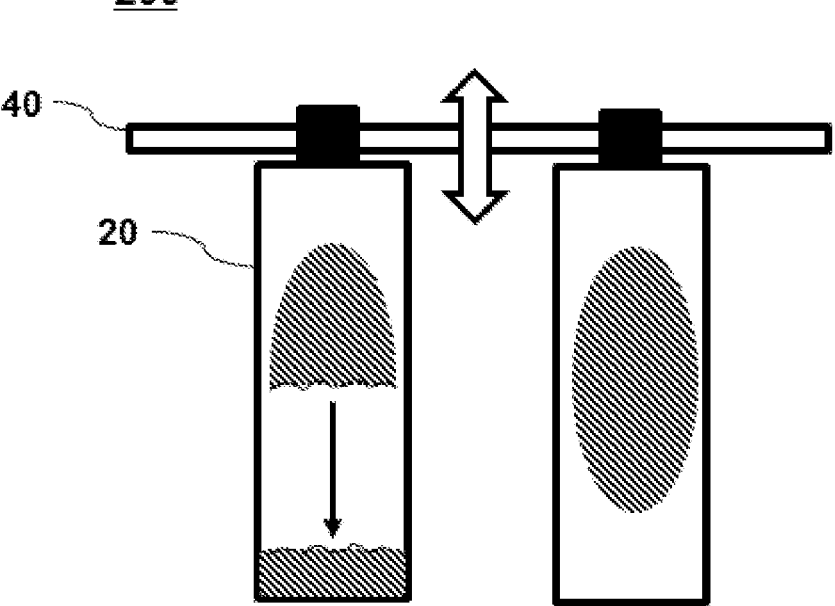

ABSORBENT ARTICLE

CROSS-REFERENCE TO RELATED APPLICATIONS

This application is a national phase entry under 35 U.S.C. § 371 of International Application No. PCT/KR2022/006773, filed on May 11, 2022, which claims the benefit of Korean Patent Application Nos. 10-2021-0060742 filed on May 11, 2021 and 10-2022-0057890 filed on May 11, 2022, the disclosures of which are incorporated herein by reference in their entirety.

TECHNICAL FIELD

The present disclosure relates to an absorbent article having excellent feeling of use due to an improved function of preventing the body fluid from leaking.

BACKGROUND ART

Absorbent articles, such as disposable diapers, sanitary napkins, incontinence pads, etc., generally include a liquid-impermeable back sheet, an absorbent body, and a liquid-permeable top sheet that comes in contact with the wearer's skin. It is known that a gather is formed in a portion that is in close contact with the circumference of the body or legs to prevent leakage of the body fluid such as urine, etc., and to improve adhesion to the human body when worn.

The gather includes an elastic body so that it can closely adhere to the wearer's body and prevents the body fluid flowing through the top sheet from leaking sideways. However, the body fluid may leak when elasticity of the elastic body decreases due to prolonged use of the article, when a lot of body fluid is released at once, or when adhesion between the gather and the body is reduced due to movement of the wearer. However, when the elasticity of the elastic body is increased in order to prevent the leakage, the wearer's body is stimulated to give discomfort.

Accordingly, it is required to develop an absorbent article that has an improved function of preventing leakage of the body fluid even when used for a long time.

DISCLOSURE

Technical Problem

There is provided an absorbent article capable of effectively preventing the body fluid from leaking to the outside.

Technical Solution

According to one embodiment of the present invention, there is provided an absorbent article including a main body portion including a liquid-impermeable back sheet, an absorbent body including a superabsorbent polymer and pulp, and a liquid-permeable top sheet, wherein the main body portion having a longitudinal direction and a width direction which are perpendicular to each other, and a pair of three-dimensional gathers disposed on two sides of the main body portion in the width direction, the pair of three-dimensional gathers extending in the longitudinal direction, wherein each three-dimensional gather of the pair of three-dimensional gathers include a gather sheet, an elastic member, and a superabsorbent polymer film with a thickness of 5 μm to 500 μm.

In the absorbent article, one end of each gather sheet is bonded with the liquid-impermeable back sheet, and another end thereof is extended outside of the main body portion and folded inward and bonded with the liquid-permeable top sheet, and the superabsorbent polymer film may be located in the space between each gather sheet, which is formed by folding each gather sheet. In this regard, the one end of the superabsorbent polymer film may be located at the bottom of the bonding portion between the liquid-permeable top sheet and each gather sheet.

The superabsorbent polymer film may have a centrifuge retention capacity of 25 g/g to 50 g/g, as measured according to the EDANA method WSP 241.2.

The superabsorbent polymer film may have a water content of 1% to 15% and a tensile strength of 9 MPa to 50 MPa.

The superabsorbent polymer film may have elongation of 100% or more, as calculated according to the following Equation 1:

$$\text{Elongation } (\%)=(L_1-L_0)/L_0*100 \qquad \text{[Equation 1]}$$

wherein in Equation 1, $L_0$ is the initial gauge length, and $L_1$ is the gauge length at the point of fracture when a specimen is tensioned at a rate of 0.5 mm per minute.

The superabsorbent polymer film may have a basis weight of 10 g/m² to 250 g/m².

The gather sheet may have a basis weight of 10 g/m² to 25 g/m².

Effect of the Invention

An absorbent article of the present disclosure exhibits an improved effect of preventing the body fluid from leaking by including a superabsorbent polymer film having excellent absorbency in three-dimensional gathers.

BRIEF DESCRIPTION OF DRAWINGS

FIG. 1 is a plan view showing an absorbent article according to an embodiment of the present invention;

FIG. 2 is a cross-sectional view of the absorbent article according to an embodiment of the present invention; and FIG. 3 is a schematic illustration of a core integrity testing device used in Experimental Example 2.

DETAILED DESCRIPTION

The terms used in this description are just for explaining exemplary embodiments and it is not intended to restrict the present invention. The singular expression may include the plural expression unless it is differently expressed contextually. It must be understood that the term "include", "equip", or "have" in the present description is only used for designating the existence of characteristics taken effect, steps, components, or combinations thereof, and do not exclude the existence or the possibility of addition of one or more different characteristics, steps, components or combinations thereof beforehand.

The present invention may be variously modified and have various forms, and specific embodiments will be illustrated and described in detail as follows. It should be understood, however, that the description is not intended to limit the present invention to the particular forms disclosed, but on the contrary, the intention is to cover all modifications, equivalents, and alternatives falling within the spirit and scope of the invention.

Likewise, the accompanying drawings to explain the present invention are shown to describe one exemplary embodiment of the present invention, and thus the present invention can be implemented in several different forms, and thus is not limited to the embodiments described herein. In order to describe embodiments of the present invention with greater clarity, certain parts irrelevant to the detailed description have been omitted in the drawings, and like parts are used to have like reference numerals throughout the specification. Also, the sizes and relative sizes of parts shown in the drawings are irrelevant to their actual scales, and may be exaggerated or diminished for the sake of convenience of description.

As used herein, the "width direction" may mean a direction having the shortest distance among straight-line distances connecting two opposing points on the perimeter of the same plane of an object, and it may also be referred to as a "horizontal direction". In addition, the "longitudinal direction" may mean a direction perpendicular to the "width direction", and may also be referred to as a "vertical direction".

An absorbent article of the present disclosure is characterized by including a superabsorbent polymer film in three-dimensional gathers to prevent the body fluid from leaking to the outside.

Specifically, the absorbent article according to one embodiment of the present invention may include a liquid-impermeable back sheet, an absorbent body including a superabsorbent polymer and pulp, and a liquid-permeable top sheet, and further including a main body portion having a longitudinal direction and a width direction which are perpendicular to each other; and a pair of three-dimensional gathers disposed on both sides of the main body portion in the width direction, the three-dimensional gathers extending in the longitudinal direction, wherein the three-dimensional gathers include a gather sheet, an elastic member, and a superabsorbent polymer film with a thickness of 5 μm to 500 μm.

FIG. 1 is a plan view showing the absorbent article according to one embodiment of the present invention. The absorbent article includes a main body portion 10 and a pair of three-dimensional gathers 20a, 20b (a three-dimensional structure not shown) disposed on both sides of the main body portion 10 in the width direction, the three-dimensional gathers extending in the longitudinal direction and wrapping around a wearer's body or legs when wearing the article. The absorbent article may also include waist band portions 30a and 30b that wrap around the wearer's waist on both sides of the main body portion 10 in the longitudinal direction.

FIG. 2 is a cross-sectional view of the absorbent article according to an embodiment of the present invention, and shows a cross-section taken along the line I-I' in FIG. 1. As shown in FIG. 2, the absorbent article of the present disclosure includes a superabsorbent polymer film 22 in a pair of three-dimensional gathers 20a, 20b disposed on both sides of the main body portion 10, respectively.

As described above, the absorbent article of the present disclosure includes the superabsorbent polymer film having a thin thickness and excellent absorbency on the outside of the main body portion including the absorbent body, thereby exhibiting a significantly improved performance of preventing leakage of the body fluid, as compared to the existing absorbent articles.

Hereinafter, respective components of the absorbent article of the present disclosure will be described in detail.
Main Body Portion In the absorbent article of the present disclosure, the main body portion 10 is a portion where absorption of the body fluid occurs, and includes a liquid-impermeable back sheet 11, an absorbent body 12 including a superabsorbent polymer and pulp, and a liquid-permeable top sheet 13. The three-dimensional gathers 20a, 20b are bonded to both sides of the main body portion 10 in the width direction.
Liquid-Impermeable Back Sheet The liquid-impermeable back sheet of the absorbent article includes an air permeable waterproof film. In order to improve softness of a material, a polyolefin nonwoven fabric manufactured by spinning an olefin-based resin such as polyethylene or polypropylene may be further included on one side of the air permeable waterproof film.

The air permeable waterproof film may be manufactured by blending a thermoplastic polymer with an additive to prepare a polymer composition, and then molding the polymer composition using a casting or expanded film extrusion technique, or other suitable film-forming technique. For example, the polymer composition may have a composition of 40% to 60% of the thermoplastic polymer and 40% to 60% of the additive. The additive may include various components depending on desired properties, such as antioxidants, filler particles, dyes, etc.

For example, the film manufactured by casting the polymer composition which is prepared by blending the thermoplastic polymer with the additive is stretched uniaxially or biaxially through three steps of a preheating process, a stretching process, and a heat setting process, thereby manufacturing the waterproof film provided with air permeability.

The thermoplastic polymer may include very low density polyethylene (VLDPE), low density polyethylene (LDPE), linear low density polyethylene (LLDPE), high density polyethylene (HDPE), polypropylene, or a copolymer of ethylene and C3-C12 alpha-olefin, a copolymer of propylene with ethylene and (or) C4-C12 alpha-olefin, a flexible polyolefin including a propylene-based polymer having both atactic and isotactic propylene units in the main polypropylene chain; elastomers, for example, polyurethanes, copolyetheresters, polyamide polyether block copolymers, ethylene vinylacetate copolymers, block copolymers such as copoly(styrene/ethylene-butylene), styrene-poly(ethylene-propylene)-styrene, styrene-poly(ethylene-butylene)-styrene, polystyrene/poly(ethylene-butylene)/polystyrene, poly(styrene/ethylene-butylene/styrene), etc., but is not limited thereto.

As the additive, a filler such as calcium carbonate ($CaCO_3$) may be used. Calcium carbonate is a white solid material produced by reacting carbonate ions with calcium ions, and may form a number of holes in the film while being combined by the polymer resin. In the present disclosure, when the air permeable waterproof film is manufactured, the content of calcium carbonate is controlled in the range of 40% by weight to 45% by weight, based on the total weight of the composition for forming the air permeable waterproof film, and a stretching ratio of the film is controlled in the range of 2.5 times to 3.5 times in the mechanical direction by considering tensile strength and moisture permeability, so that the size of holes formed in the film is controlled. As a result, excrement absorbed by the absorbent body does not leak to the outside while allowing air or vapor more freely to pass through the back sheet.

Specifically, when the content of calcium carbonate and the stretching ratio of the film are controlled within the above-described ranges, holes having a size (diameter) of about 10 μm to 90 μm, preferably, about 40 μm to 60 μm may be formed in the film. The size of these holes is smaller than the size of water particles of 100 μm or more, and larger than the size of vapor, which is about 0.001 μm to 0.01 μm. Therefore, the excrement absorbed by the absorbent body does not leak to the outside due to the air permeable waterproof film, while easily discharging the hot air or vapor inside the diaper to the outside through the air permeable waterproof film.

The air permeable waterproof film may have air permeability in the range of 2000 g/m²·0.24 hr to 5000 g/m²·0.24 hr, preferably 3500 g/m²·0.24 hr to 4500 g/m²·0.24 hr. When air permeability satisfies the above range, it is possible to more effectively prevent skin trouble from occurring due to humid air.

When the air permeable waterproof film may have, but is not particularly limited to, a basis weight of about 15 g/m² to 22 g/m², the strength of the film may be more improved, and air permeability of the film may be controlled in the range of about 3500 g/m²·0.24 hr to about 4500 g/m²·0.24 hr, and thus the excrement absorbed by the absorbent core may be blocked from leaking to the outside, air or vapor may be easily discharged through the back sheet to further improve the wearer's comfort of wearing.

The polyolefin nonwoven fabric serves to improve the air permeability of the back sheet and softness of the material. A method of manufacturing the nonwoven fabric is not particularly limited, and those manufactured by a processing method, such as air-laying, thermal bonding, spun lacing, spun bonding, melt blowing, stitch bonding, etc., may be used without limitation.

The polyolefin nonwoven fabric may have a pore size of 20 μm to 1000 μm, 50 μm to 700 μm, or 10 μm to 300 μm. When the pore size of the nonwoven fabric satisfies the above range, permeation of liquid is blocked and permeation of vapor and air is possible, thereby exhibiting excellent comfort of wearing.

The basis weight of the polyolefin nonwoven fabric is not particularly limited. However, when it is about 10 g/m² to about 25 g/m², preferably, about 12 g/m² to about 20 g/m², the excrement absorbed in the absorbent body does not leak to the outside while further improving the feel.

Absorbent Body

The absorbent body used in the absorbent article of the present disclosure includes a superabsorbent polymer powder which is an aggregate of superabsorbent polymer particles, and pulp.

As the superabsorbent polymer powder, a material usually used for imparting absorption performance to the absorbent article may be used without limitation. The superabsorbent polymer may be, for example, one or more selected from the group consisting of a crosslinked product of an acrylate polymer, a crosslinked product of a vinyl alcohol-acrylate copolymer, a crosslinked product of a maleic anhydride-grafted polyvinyl alcohol, a crosslinked product of an acrylate-methacrylate copolymer, a crosslinked product of a saponification product of a methyl acrylate-vinyl acetate copolymer, a crosslinked product of a starch-acrylate grafted copolymer, a crosslinked product of a saponification product of starch-acrylonitrile grafted copolymer, a crosslinked product of carboxymethylcellulose, a crosslinked product of an isobutylene-maleate anhydride copolymer, and a cross-linked product of methylene oxide polymer, and preferably, a crosslinked product of an acrylate polymer.

The size of the superabsorbent polymer particles constituting the superabsorbent polymer powder may be 100 μm to 1,000 μm, 150 μm to 800 μm, or 300 to 600 μm. When the size of the superabsorbent polymer particles is less than 100 μm, it is apprehended that the superabsorbent polymer gel swelled by absorbing the body fluid may be discharged to the outside of the absorbent article, or physical properties may be deteriorated due to a gel blocking phenomenon, and when the particle size exceeds 1,000 μm, there is a problem in that it is difficult to slim the absorbent article.

The superabsorbent polymer powder may be included in an amount of 10% by weight to 90% by weight, preferably, in an amount of 20% by weight or more, 30% by weight or more, or 40% by weight or more, and 80% by weight or less, or 60% by weight or less, based on the total weight of the absorbent body.

The pulp used in the absorbent body may be cellulose fluff pulp produced by pulverizing wood pulp. The pulp may quickly absorb liquid and may act to separate superabsorbent polymer particles from each other to reduce gel adhesion.

In order to secure such an effect, the pulp may be included in an amount of 10% by weight to 90% by weight, preferably, in an amount of 20% by weight or more, or 40% by weight or more, and 80% by weight or less, 70% by weight or less, or 50% by weight or less, based on the total weight of the absorbent body.

Specifically, the superabsorbent polymer may be included in an amount of about 10% by weight to about 90% by weight, preferably, in an amount of 30% by weight to 60% by weight, based on the total weight of the absorbent body, and the pulp is included in an amount of about 10% by weight to about 90% by weight, preferably, in an amount of about 40% by weight to about 70% by weight, based on the total weight of the absorbent body.

In addition to the superabsorbent polymer powder and pulp, the absorbent body may optionally further include synthetic fibers such as polyethylene fibers, polypropylene fibers, polyester fibers, polyamide fibers, rayon fibers, polyurethane fibers, etc., and in this case, the bonding force between the superabsorbent polymer powder and the pulp may be further improved. These synthetic fibers may be used in an amount of 20% by weight or less, or 10% by weight or less, based on the total weight of the absorbent body.

A method of manufacturing the absorbent body is not particularly limited. For example, the superabsorbent polymer powder and pulp, optionally, the synthetic fiber may be uniformly mixed, and molded by applying heat, pressure, etc., and then the molded article may be packaged using a packaging material such as a tissue, etc., thereby manufacturing the absorbent body.

Liquid-Permeable Top Sheet

In the liquid-permeable top sheet, a material that has hydrophilicity to allow liquid to quickly pass therethrough, feels soft, and does not irritate the user's skin.

The liquid-permeable top sheet may be, for example, a hydrophilic nonwoven fabric, an apertured film such as an apertured polyethylene film, etc., or a foamed film such as urethane foam, etc., and a laminate of one or more thereof may be used.

Preferably, the liquid-permeable top sheet may be a hydrophilic nonwoven fabric manufactured using synthetic fibers or natural fibers, such as polypropylene, polyethylene, polyester, polyethylene terephthalate, rayon, cotton, cotton wool, etc. A method of manufacturing the nonwoven fabric is not particularly limited, and those manufactured by a processing method, such as air through, air-laying, thermal bonding, spun lacing, spun bonding, melt blowing, stitch bonding, etc., may be used without limitation.

The fiber thickness (fineness) of the liquid-permeable nonwoven fabric is not particularly limited. However, when the fiber thickness is in the range of about 1.5 denier to about 6 denier (d), preferably, about 1.5 denier to about 2 denier (d), skin irritation is minimized upon wearing the absorbent article, thereby minimizing occurrence of skin troubles and improving the instantaneous absorption function.

In addition, the length of the fiber is not particularly limited. However, when it is about 36 mm to about 39 mm, workability of a carding process may be improved during manufacturing the nonwoven fabric, and the surface evenness of the nonwoven fabric may be improved to minimize friction with the wearer's skin.

The basis weight of the nonwoven fabric made of these fibers is not particularly limited. However, when it is about 15 g/m$^2$ to about 30 g/m$^2$, preferably, about 15 g/m$^2$ to about 20 g/m$^2$, absorption power may be improved and the surface texture may be made softer, thereby minimizing occurrence of the skin troubles.

A method of manufacturing the main body portion is not particularly limited, but the main body portion may be manufactured by laminating the liquid-impermeable back sheet, the absorbent body, and the liquid-permeable top sheet in an appropriate order and then fixing them with embossing, or fixing the respective components using an adhesive such as a hot melt adhesive, etc. In this case, the liquid-impermeable back sheet, the absorbent body, and the liquid-permeable top sheet may be configured such that the areas thereof may be the same as or different from each other.

Three-Dimensional Gather

The three-dimensional gathers 20a, 20b are band-shaped members that extends along both sides of the main body portion 10 in the front and rear directions and are formed to stand on the surface side, i.e., the wearer's skin surface side, and are formed to block urine or soft stool that moves in the horizontal direction along the liquid-permeable top sheet 13, thereby preventing it from leaking sideways.

Since the three-dimensional gathers 20a, 20b stand on the surface side, a space is created between the three-dimensional gathers 20a, 20b and the main body portion 10 upon wearing, and thus excrement is physically prevented from leaking out. However, excrement may leak out of the three-dimensional gathers 20a, 20b when the wearer excessively moves or when a large amount of excrement is excreted at once. Therefore, the absorbent article according to one embodiment of the present invention includes a superabsorbent polymer film 22 in the three-dimensional gathers 20a, 20b, such that the excrement flowing into the space between the three-dimensional gathers 20a, 20b and the main body portion 10 may be absorbed immediately before it moves and leaks out.

The three-dimensional gathers 20a, 20b have a structure, in which each gather sheet 21 extends outward from the side of the main body portion 10 and is folded inward again, and an elastic member 23 and the superabsorbent polymer film 22 are placed in the space formed by folding each gather sheet 21, i.e., a structure, in which the elastic member 23 and the superabsorbent polymer film 22 are included in the space between each gather sheet 21.

The three-dimensional gather having the structure may be formed by bonding one end of the band-shaped gather sheet 21 having the same length as the length of the main body portion 10 to the side of the main body portion 10, folding the other unbonded end in the width direction to overlap two ends, and then bonding the other end of the gather sheet 21 to the side of the main body portion 10 again. At this time, one end of the gather sheet 21 may be bonded to the liquid-impermeable back sheet 11, and the other end thereof may be bonded to the liquid-permeable top sheet 13.

In this specification, the portion where the main body portion 10 and the gather sheet 21 are bonded is referred to as a proximal end portion 21a of the three-dimensional gather, and the portion where the gather sheet 21 is folded inward is referred to as a distal end portion 21b of the three-dimensional gather.

The superabsorbent polymer film 22 may be included in any position inside the three-dimensional gathers 20a, 20b, but it is preferably located at the proximal end portion 21a of the three-dimensional gathers 20a, 20b. Specifically, one end of the superabsorbent polymer film 22 is preferably located at the lower end of the bonding portion between the liquid-permeable top sheet 13 and the gather sheet 21, i.e., the portion where the two sheets overlap. In this case, when the body fluid flowing through the upper sheet 13 stays in the space between the three-dimensional gathers 20a and 20b and the main body portion, it may be quickly absorbed into the superabsorbent polymer film 22 through the liquid-permeable top sheet 13 of the proximal end portion 21a, thereby exhibiting an excellent leakage prevention effect.

Alternatively, as shown in FIG. 2, one end of the superabsorbent polymer film 22 is disposed to further extend to the outside of the proximal end portion 21a of the three-dimensional gathers 20a and 20b, i.e., to the main body portion side such that the superabsorbent polymer film 22 is allowed to be positioned immediately below the liquid-permeable top sheet 13 of the main body portion, thereby further improving the leakage prevention effect.

The superabsorbent polymer film 22 may be extended from the proximal end portion 21a of the three-dimensional gathers 20a, 20b up to the distal end portion 21b in the width direction, and may be extended by the length of the three-dimensional gathers 20a, 20b in the longitudinal direction.

The position between the elastic member and the superabsorbent polymer film 22 in the three-dimensional gathers 20a, 20b is not particularly limited. The elastic member may be disposed in a portion of the three-dimensional gathers 20a, 20b, where the superabsorbent polymer film 22 does not exist, and/or the elastic member may be disposed between the superabsorbent polymer film (22) and the gather sheet (21).

The three-dimensional gathers 20a, 20b of one embodiment are provided so as to stand upright from the side of the main body portion, as shown in FIG. 2, and the root-side portion stands obliquely toward the center-side in the width direction, and the portion closer to the tip side than the intermediate portion stands obliquely toward the outside in the width direction. The tip side of the three-dimensional gathers 20a, 20b is in close contact with the body, and the space between the main body portion and the three-dimensional gathers 20a, 20b is better maintained, so that the excrement does not leak out and may be transferred and absorbed into the superabsorbent polymer film 22 in the three-dimensional gathers 20a, 20b.

The standing height (h) of the three-dimensional gathers 20a and 20b, i.e., the height protruding from the bottom surface (back sheet surface) of the article when the absorbent article is unfolded may be 20 mm to 50 mm, or 30 mm to 40 mm. In addition, the length of the three-dimensional gathers 20a, 20b may be adjusted according to the length of the main body portion 10 and the absorbent article, for example, may be formed in a length of 400 mm to 500 mm, or 400 to 450 mm. At this time, the length of the elastic member and the superabsorbent polymer film 22 interposed between the gather sheets 21 may be the same as the length of the three-dimensional gathers 20a, 20b, or may be formed shorter.

Gather Sheet

The gather sheet 21 is preferably hydrophobic to prevent leakage of the body fluid.

The gather sheet may be a nonwoven fabric manufactured from an olefin-based resin such as polyethylene, polypropylene, etc. As a method of manufacturing the nonwoven fabric, a common processing method, such as air-laying, thermal bonding, spun lacing, spun bonding, melt blowing, stitch bonding, etc., may be used without limitation. In addition, SMS nonwoven fabrics, SMMMS nonwoven fabrics, SSMMS nonwoven fabrics, etc., which are complex nonwoven fabrics of spunbond nonwoven fabrics and melt blown nonwoven fabrics, may be used. For example, as the gather sheet, a hydrophobic SMS polypropylene nonwoven fabric may be used.

The gather sheet may have a basis weight of 10 g/m² to 25 g/m², preferably, 12 g/m² to 20 g/m². Within the above range, the excellent effects of preventing leakage and improving adhesion to the skin may be obtained.

The gather sheet may be prepared separately from the main body portion, and then bonded to the side of the main body portion. The bonding method is not particularly limited, and thermal bonding or a bonding method using an adhesive may be used.

Alternatively, the liquid-impermeable back sheet of the main body portion may be extended, which may be used as the gather sheet. That is, when the width of the liquid-impermeable back sheet is wider than the width of the absorbent body and the liquid-permeable top sheet, the extra edge of the liquid-impermeable back sheet may be used as the gather sheet.

Elastic Member

The elastic member 23 is included to improve adhesion to the body, and one or more, preferably, three to five elastic members may be included in each of the three-dimensional gathers 20a, 20b.

For example, as the elastic member, a thin and long spandex thread rubber may be used. The thickness of the spandex thread rubber may be 450 dtex to 1200 dtex, or 600 dtex to 900 dtex, and the elongation when fixed may be in the range of 150% to 300%, or 200% to 300%.

The elastic member may be pre-bonded with the gather sheet. In other words, the elastic member is bonded to one side of the gather sheet, which is folded such that the surface, to which the elastic member is bonded, comes into contact to form the three-dimensional gathers.

Alternatively, the elastic member is prepared separately from the gather sheet, and appropriately arranged with the superabsorbent polymer film, and then fixed with the gather sheet to form the three-dimensional gather.

Superabsorbent Polymer Film

To more effectively prevent leakage of the body fluid, the three-dimensional gathers include the superabsorbent polymer film 22 having a thin thickness and excellent absorbency.

The superabsorbent polymer film exhibits excellent absorption performance while being thin. Therefore, when the superabsorbent polymer film is included in the three-dimensional gathers, it is possible to effectively prevent the body fluid from leaking to the outside without causing discomfort to the wearer. In addition, since the superabsorbent polymer film has excellent mechanical properties such as tensile strength, elongation, etc., it may effectively prevent leakage of the body fluid without being easily damaged even when the wearer moves.

The superabsorbent polymer film is an acrylic acid-based polymer in the form of a thin film which is distinct from the particulate superabsorbent polymer included in the absorbent body, and it indicates a superabsorbent polymer having a water content of 15% or less, being colorless, transparent, having elasticity, and being in the form of a film having excellent flexibility. The superabsorbent polymer film has no concern about scattering or leaking from the absorbent article during handling, and may be used as the absorbent body itself without aids such as pulp, etc.

Preferably, the water content of the superabsorbent polymer film may be 15% by weight or less, or 12% by weight or less, or 11% by weight or less, or 10% by weight or less, and 1% by weight or more, or 2% by weight or more, or 4% by weight or more, or 6% by weight.

The "water content" is expressed as a percentage of the amount of water contained in a sample with respect to the weight of the sample before drying. In other words, the water content may be calculated by dividing a value, which is obtained by subtracting the weight of the sample after drying from the weight of the sample before drying, by the weight of the sample before drying, and then multiplying by 100. At this time, the drying conditions are determined as follows: the temperature is increased from room temperature to about 150° C. and then the temperature is maintained at 150° C., and the total drying time is set to 20 minutes, including 5 minutes for the temperature rising step.

The superabsorbent polymer film has a thickness of 5 μm to 500 μm, and in this range of thickness, the total light transmittance for visible light is 89.5%, indicating high transparency. The total light transmittance of the superabsorbent polymer film according to an embodiment of the present invention may be 90% or more, 90.3% or more, or 91% or more, or 91.5% or more, or 92% or more. The total light transmittance may be theoretically 100%, for example, 99% or less.

In addition, the superabsorbent polymer film of the present disclosure has a yellowness index of 2.6 or less, 2.5 or less, 2.4 or less, 2.3 or less, 1.9 or less, 1.5 or less, or 1.3 or less according to ASTM D1925 standard in the thickness range of 1 μm to 500 μm.

Since the superabsorbent polymer film has a thin thickness of 500 μm or less, it is possible to provide a function of preventing leakage of the body fluid without significantly increasing the thickness of the three-dimensional gather. In addition, when the thickness of the superabsorbent polymer film exceeds 500 μm, air permeability may decrease. However, in the thin superabsorbent polymer film of 500 μm or less, flexibility of the film greatly increases when water is absorbed, and the space between polymer chains increases. Thus, it may exhibit the effect of preventing leakage of the body fluid while ensuring air permeability. As a result, the three-dimensional gathers including the superabsorbent polymer film may maintain a thin thickness, and thus adhesion to the body is not reduced, and the wearer does not feel discomfort due to feeling of irritation or reduced air permeability while exhibiting the excellent function of preventing leakage of the body fluid.

From this point of view, the thickness (h) of the superabsorbent polymer film may be preferably 5 μm or more, 10 μm or more, or 15 μm or more, and 400 μm or less, 300 μm or less, 200 μm or less, or 150 μm or less.

The superabsorbent polymer film exhibits excellent absorption performance while having a thin thickness, thereby effectively preventing the body fluid from leaking.

For example, the superabsorbent polymer film exhibits excellent absorption properties with centrifuge retention capacity (CRC) of 25 g/g or more, 30 g/g or more, or 34 g/g or more, as measured according to the EDANA method WSP 241.2. Centrifuge retention capacity is superior as the value is higher, and therefore, although there is no theoretical upper limit, it may be, for example, 50 g/g or less, or 48 g/g or less.

In addition, the superabsorbent polymer film may have absorbency under pressure (AUP) of 0.7 psi of 5.0 g/g or more, 7.0 g/g or more, or 9.0 g/g or more, and 25 g/g or less, or 20 g/g or less, as measured according to the EDANA method WSP 242.2.

Meanwhile, the superabsorbent polymer film may have the water content of 1% to 15%, and tensile strength of 5 MPa or more. Preferably, when the water content is 5% to 15%, the tensile strength of the superabsorbent polymer film may be 10 MPa or more, 13 MPa or more, 14 MPa or more, 19 MPa or more, or 22 MPa or more, and 50 MPa or less, 47 MPa or less, 45 MPa or less, 40 MPa or less, or 35 MPa or less. As described, as the superabsorbent polymer film exhibits high tensile strength, it may exhibit the excellent function of preventing leakage of the body fluid without being easily damaged even when the wearer moves.

In addition, since the superabsorbent polymer film has excellent flexibility and elasticity, it is suitable for being applied to the three-dimensional gathers. For example, the superabsorbent polymer film may have an elongation of 100% or more, 120% or more, 150% or more, 180% or more, or 200% or more, and 550% or less, 530% or less, or 510% or less, as calculated according to the following Equation 1. Therefore, the superabsorbent polymer film may exhibit the excellent absorption performance without being easily damaged even when applied to the three-dimensional gather with a lot of movement.

$$\text{Elongation } (\%) = (L_1 - L_0)/L_0 * 100 \qquad \text{[Equation 1]}$$

in Equation 1,
$L_0$ is the initial gauge length, and
$L_1$ is the gauge length at the point of fracture when a specimen is tensioned at a rate of 0.5 mm per minute.

The size of the superabsorbent polymer film included in the three-dimensional gather may be appropriately adjusted according to the size and configuration of the absorbent article and the three-dimensional gathers.

However, when the weight per unit area of the superabsorbent polymer film is too high, deformation may occur, such as sagging of the three-dimensional gathers due to the absorbed body fluid. On the contrary, when the superabsorbent polymer film is included in the excessively small amount, it is difficult to expect the sufficient effect of preventing leakage of the body fluid. Thus, it is preferable that the basis weight of the superabsorbent polymer film satisfies the range of 10 g/m² or more, 20 g/m² or more, or 22 g/m² or more, and 250 g/m² or less, 230 g/m² or less, or 215 g/m² or less.

The above-described superabsorbent polymer film may be manufactured by a method of including the steps of preparing a monomer composition by mixing an acrylic acid-based monomer having an acidic group of which at least a part is neutralized, a cellulose-based thickener, a moisturizing agent, an internal crosslinking agent, a polymerization initiator, and a solvent; forming a monomer composition film by casting the monomer composition on a substrate; forming a water-containing gel polymer film by irradiating heat and/or light while stretching the monomer composition film; and drying the water-containing gel polymer film.

According to the manufacturing method, the film-type superabsorbent polymer may be produced by manufacturing the monomer composition film from the monomer composition solution having a controlled viscosity through a solution casting method, and then polymerizing and drying the same. In particular, the monomer composition film may be stretched by applying a tension thereto in the polymerization step, and thus it is possible to control the tensile strength of the superabsorbent polymer film to be manufactured.

Hereinafter, the method of manufacturing the superabsorbent polymer film will be described in detail.

The monomer composition may include an acrylic acid-based monomer having an acidic group of which at least a part is neutralized, a cellulose-based thickener, a moisturizing agent, a polymerization initiator, and a solvent.

First, the acrylic acid-based monomer is a compound represented by the following Formula 1:

$$R^1\text{—COOM}^1 \qquad \text{[Formula 1]}$$

in Formula 1,
$R^1$ is an alkyl group containing an unsaturated bond and having 2 to 5 carbon atoms, and
$M^1$ is a hydrogen atom, a monovalent or divalent metal, an ammonium group, or an organic amine salt.

Preferably, the acrylic acid-based monomer may include one or more selected from the group consisting of acrylic acid, methacrylic acid, and a monovalent metal salt thereof, a divalent metal salt thereof, an ammonium salt thereof, and an organic amine salt thereof.

Here, the acrylic acid-based monomer may have an acidic group, of which at least a part may be neutralized. Preferably, those partially neutralized with an alkaline substance such as sodium hydroxide, potassium hydroxide, ammonium hydroxide or the like may be used as the monomer. In this regard, the degree of neutralization of the acrylic acid-based monomer may be 40 mol % to 95 mol %, or 40 mol % to 80 mol %, or 45 mol % to 75 mol %. The range of the degree of neutralization may vary depending on the final physical properties. An excessively high degree of neutralization causes the neutralized monomers to be precipitated, and thus polymerization may not readily occur. On the contrary, an excessively low degree of neutralization may greatly deteriorate the absorbency of the polymer.

In one preferred embodiment, potassium hydroxide (KOH) may be used as the alkaline substance. When potassium hydroxide is used, it is preferable because a superabsorbent polymer film having flexibility and dimensional stability is manufactured even when the water content is 10% or less.

The concentration of the acrylic acid-based monomer may be about 20% by weight to about 60% by weight, preferably about 40% by weight to about 50% by weight with respect to the monomer composition including raw materials of the superabsorbent polymer and solvents, and the concentration may be appropriately controlled by considering a polymerization time, reaction conditions, etc. When the concentration of the monomer is too low, the yield of the superabsorbent polymer may become low, and there may be a problem in terms of economic efficiency. On the contrary, when the concentration of the monomer is too high, there is a process problem in that part of the monomers is precipitated, and the physical properties of the superabsorbent polymer may deteriorate.

Meanwhile, in the present disclosure, a thickener and a moisturizing agent are included in the monomer composition so that the monomer composition may be applied in a film type through a solution casting method.

As described, when the thickener and the moisturizing agent are included at the same time, the monomer composition of the present disclosure may exhibit a viscosity suitable for casting into the film type and may maintain an appropriate water content in the polymerization process after film casting, and the produced superabsorbent polymer film may exhibit high flexibility.

In the present disclosure, a cellulose-based thickener is used as the thickener, and specifically, one or more selected from the group consisting of nanocellulose, hydroxyethylcellulose, hydroxypropylcellulose, hydroxyethylmethylcellulose, and hydroxypropylmethylcellulose may be used. Preferably, nanocellulose, hydroxyethylcellulose, or a combination thereof may be used.

The cellulose-based thickener may be included in an amount of 0.01 part by weight or more, 0.1 part by weight or more, 0.2 parts by weight or more, or 0.35 parts by weight or more, and 5 parts by weight or less, 3 parts by weight or less, 1 part by weight or less, or 0.9 parts by weight or less, based on 100 parts by weight of the solid content in the monomer composition.

At this time, the solid content in the monomer composition means all components of the composition, excluding the solvent. In other words, the solid content means the total content of the acrylic acid-based monomer, the alkaline substance for neutralizing the acrylic acid-based monomer, the cellulose-based thickener, the moisturizing agent, a crosslinking agent, a thermal initiator, a photo-initiator, an internal crosslinking agent, and other additives.

When the content of the cellulose-based thickener is less than 0.01 part by weight, based on 100 parts by weight of the solid content in the monomer composition, it may be difficult to manufacture the monomer composition film because a sufficient thickening effect may not be secured. On the contrary, when the content exceeds 5 parts by weight, viscosity of the monomer composition becomes too high, and thickness of the film becomes thick, and it may be difficult to uniformly control the thickness of the film.

As the moisturizing agent, a substance usually used as a moisturizing component in pharmaceuticals, cosmetics, chemical products, etc. may be used without limitation. Examples of such a moisturizing agent may include one or more selected from the group consisting of polyhydric alcohols containing two or more hydroxyl groups in the molecule, citric acid, and citrate.

Specifically, as the polyhydric alcohol, a polyhydric alcohol having 3 to 30 carbon atoms and including 3 to 12 hydroxyl groups in the molecule may be used. For example, the polyhydric alcohol may be one or more selected from the group consisting of glycerin; diglycerin; propylene glycol; butylene glycol; sorbitol; polyethylene glycol; polyglycerin-3; polyglycerin-6; polyglycerin-10; and polyglyceryl-10 distearate and derivatives thereof (3 to 18 carbon atoms), and among them, one or more selected from the group consisting of glycerin, diglycerin, ethylene glycol, and sorbitol may be preferably used.

Further, citric acid and/or citrate may be used as the moisturizing agent. Examples of the citrate may include triethyl citrate, methyl citrate, sodium citrate, trisodium 2-methyl citrate, etc.

The moisturizing agent is preferably used in an amount of 5 parts by weight or more, 10 parts by weight or more, 20 parts by weight or more, or 30 parts by weight or more, and 70 parts by weight or less, 60 parts by weight or less, or 50 parts by weight or less, based on 100 parts by weight of the acrylic acid-based monomer.

When the content of the moisturizing agent is less than 5 parts by weight, based on 100 parts by weight of the acrylic acid-based monomer, there are problems in that the water content of the monomer composition film is not sufficient, and the film may dry out or crumble in the subsequent polymerization and drying processes, and flexibility of the manufactured superabsorbent polymer film may not be secured. On the contrary, when the content of the polyhydric alcohol exceeds 70 parts by weight, based on 100 parts by weight of the acrylic acid-based monomer, there is a problem in that the absorption capacity of the superabsorbent polymer film may be reduced. Therefore, it is preferable that the content of the moisturizing agent satisfies the above range.

The monomer composition includes an internal crosslinking agent for crosslinking the polymer. As the internal crosslinking agent, those commonly used in the preparation of the superabsorbent polymer may be used. More specifically, as the internal crosslinking agent, a crosslinking agent having one or more functional groups reactable with a water-soluble substituent of the acrylic acid-based monomer and one or more ethylenically unsaturated groups; or a crosslinking agent having two or more functional groups reactable with a water-soluble substituent of the monomer and/or a water-soluble substituent formed by hydrolysis of the monomer may be used.

Specific examples of the internal crosslinking agent may include one or more selected from the group consisting of bisacrylamide having 8 to 12 carbon atoms, bismethacrylamide, poly(meth)acrylate of a polyol having 2 to 10 carbon atoms, or poly(meth)allyl ether of a polyol having 2 to 10 carbon atoms. More specific examples thereof may include one or more selected from the group consisting of N,N'-methylene bis(meth)acrylate, ethyleneoxy(meth)acrylate, polyethyleneoxy(meth)acrylate, propyleneoxy(meth)acrylate, glycerin diacrylate, glycerin triacrylate, trimethyloltriacrylate, polyethylene glycol diacrylate, triallylamine, triarylcyanurate, triallylisocyanate, polyethylene glycol, diethylene glycol, and propylene glycol. In one embodiment, as the internal crosslinking agent, polyethylene glycol diacrylate may be used.

The internal crosslinking agent may be included at a concentration of 5000 ppm or less, based on the monomer composition, thereby crosslinking the polymerized polymer. In one embodiment, the internal crosslinking agent may be included in an amount of 100 ppm or more, 250 ppm or more, or 500 ppm or more, and 5000 ppm or less, 4500 ppm or less, or 4000 ppm or less. The content of the internal crosslinking agent may be appropriately adjusted, depending on the thickness of the manufactured superabsorbent polymer film and the desired range of tensile strength.

As a polymerization initiator used during polymerization in the method of manufacturing the superabsorbent polymer film of the present disclosure, those generally used in the preparation of superabsorbent polymers may be used without particular limitation.

Specifically, the polymerization initiator may be a thermal polymerization initiator or a photo-polymerization initiator by UV irradiation, depending on the polymerization method. However, even in the case of using the photo-polymerization method, a certain amount of heat is generated by the ultraviolet irradiation or the like, and a certain degree of heat is also generated according to the progress of the exothermic polymerization reaction, and therefore, a thermal polymerization initiator may be additionally included. In one preferred embodiment, the photo-polymerization initiator and the thermal polymerization initiator may be used at the same time as the polymerization initiator.

The photo-polymerization initiator may be used without limitation in view of constitution as long as it is a compound capable of forming a radical by light such as UV ray.

The photo-polymerization initiator may include, for example, one or more selected from the group consisting of benzoin ether, dialkyl acetophenone, hydroxyl alkylketone, phenyl glyoxylate, benzyl dimethyl ketal, acyl phosphine, and α-aminoketone. Meanwhile, specific examples of the acyl phosphine may include commercially available lucirin TPO (2,4,6-trimethylbenzoyldiphenylphosphine oxide), Irgacure 819 (phenylbis(2,4,6-trimethylbenzoyl)phosphine oxide), etc. More various photo-polymerization initiators are well disclosed in "UV Coatings: Basics, Recent Developments and New Application (Elsevier, 2007)" written by Reinhold Schwalm, p 115, however, the photo-polymerization initiator is not limited to the above-described examples.

The photo-polymerization initiator may be included at a concentration of 10 ppm or more, 20 ppm or more, or 40 ppm or more, and 2000 ppm or less, 1000 ppm or less, 500 ppm or less, or 100 ppm or less with respect to the monomer composition. When the concentration of the photo-polymerization initiator is too low, the polymerization rate may become slow, and when the concentration of the photo-polymerization initiator is too high, a molecular weight of the superabsorbent polymer becomes small and its physical properties may become uneven.

Further, as the thermal polymerization initiator, one or more initiators selected from the group consisting of a persulfate-based initiator, an azo-based initiator, hydrogen peroxide, and ascorbic acid may be used. Specific examples of the persulfate-based initiator may include sodium persulfate ($Na_2S_2O_8$), potassium persulfate ($K_2S_2O_8$), ammonium persulfate (($NH_4)_2S_2O_8$), etc., and examples of the azo-based initiator may include 2,2-azobis-(2-amidinopropane) dihydrochloride, 2,2-azobis-(N,N-dimethylene)isobutyramidine dihydrochloride, 2-(carbamoylazo)isobutyronitrile, 2,2-azobis[2-(2-imidazolin-2-yl)propane]dihydrochloride, 4,4-azobis-(4-cyanovaleric acid), etc. More various thermal polymerization initiators are well disclosed in 'Principle of Polymerization (Wiley, 1981)' written by Odian, p 203, however, the thermal polymerization initiator is not limited to the above-described examples.

The thermal polymerization initiator may be included at a concentration of 10 ppm or more, 100 ppm or more, or 500 ppm or more, and 2000 ppm or less, 1500 ppm or less, or 1000 ppm or less with respect to the monomer composition. When the concentration of the thermal polymerization initiator is too low, additional thermal polymerization hardly occurs, and thus effects due to the addition of the thermal polymerization initiator may be insignificant, and when the concentration of the thermal polymerization initiator is too high, the molecular weight of the superabsorbent polymer becomes small and the physical properties may become uneven.

The monomer composition may further include additives such as a plasticizer, a storage stabilizer, and an antioxidant, as needed.

The raw materials such as the above-described acrylic acid-based unsaturated monomer, cellulose-based thickener, moisturizing agent, internal crosslinking agent, polymerization initiator, and additive may be prepared in the form of a monomer composition solution in which the raw materials are dissolved in a solvent.

As the solvent to be applicable, any solvent may be used without limitations in view of constitution as long as it is able to dissolve the above components, and for example, one or more selected from water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methyl ethyl ketone, acetone, methyl amyl ketone, cyclohexanone, cyclopentanone, diethylene glycol monomethyl ether, diethylene glycol ethylether, toluene, xylene, butyrolactone, carbitol, methyl cellosolve acetate, and N,N-dimethylacetamide may be used in combination. For example, water may be used as the solvent.

In the present disclosure, the monomer composition exhibits a viscosity suitable for a solution casting method by including the cellulose-based thickener and the moisturizing agent. Specifically, the viscosity at 25° C. of the monomer composition may be 100 mPa·s or more, 140 mPa·s or more, or 200 mPa·s or more, and 5000 mPa·s or less, 2300 mPa·s or less, 2000 mPa·s or less, 1500 mPa·s or less, or 1400 mPa·s or less. The viscosity of the monomer composition may be measured with a viscometer (e.g., TV-22 manufactured by TOKI Corporation) under the conditions of spindle #1 and a rotational speed of 1 rpm.

When the viscosity of the monomer composition is less than 100 mPa·s, it may be difficult to perform polymerization while casting the monomer composition film to a uniform thickness and stretching the same. On the contrary, when the viscosity of the monomer composition exceeds 5000 mPa·s, it is difficult to prepare a uniform monomer composition, and processability is lowered due to poor flowability of the monomer composition, and defoaming is difficult, which are not preferred.

After preparing the monomer composition, it is casted on a substrate to manufacture the monomer composition film, and the film is polymerized while being stretched to form a water-containing gel polymer film. Casting and polymerization of the monomer composition may be continuously performed through a roll-to-roll process.

First, the monomer composition is applied on the substrate to manufacture the monomer composition film.

Generally, in a polymer solution casting method, the solvent is removed after casting the polymer solution. In contrast, in the present disclosure, the monomer composition is applied on the substrate, and then the stretching and polymerization processes are performed immediately to prevent a reduction of the water content.

When the water content of the monomer composition film is too low, there are problems in that components constituting the monomer composition may be precipitated before polymerization, and the film may be broken after polymerization. Accordingly, it is preferable that the water content of the monomer composition film satisfies the range of 30% by weight to 60% by weight, and the range of 30% by weight to 50% by weight, or 30% by weight to 45% by weight.

The thickness of the monomer composition film may be appropriately adjusted according to the desired thickness of the superabsorbent polymer film. Although the thickness of the monomer composition film hardly changes during the polymerization stage, the thickness may decrease by about 10% to 40%, or 15% to 35% as the water content decreases during the process of drying the water-containing gel polymer film after polymerization. In consideration of this, the monomer composition film is manufactured in an appropriate thickness.

For example, the thickness of the monomer composition film may be 800 μm or less, 600 μm or less, or 500 μm or less, and 1 μm or more, 5 μm or more, or 10 μm or more, but is not limited thereto. The thickness may be appropriately adjusted according to the composition of the monomer composition or specific conditions in the polymerization and drying steps, and the desired thickness of the superabsorbent polymer film.

Next, polymerization is performed by irradiating heat and/or light while stretching the monomer composition film in the longitudinal direction (MD direction), thereby forming the water-containing gel polymer film. As described, when the film is polymerized while being stretched, physical properties of the manufactured superabsorbent polymer film, such as tensile strength, may be controlled.

At this time, the tension applied to the monomer composition film may be 40 N/m or more, or 45 N/m or more, or 50 N/m or more, or 60 N/m or more, and 100 N/m or less, or 90 N/m or less, or 70 N/m or less. When the film is stretched by applying an excessively large tension, there is a problem in that the monomer composition film is broken or the thickness becomes excessively thin, and when the tension is too small, physical properties of the film, such as tensile strength, etc., may not be secured.

The polymerization temperature may be appropriately adjusted depending on the composition of the monomer composition, but is preferably 40° C. or 50° C. or higher for smooth reaction progress. In addition, when the temperature is too high, the solvent evaporates, leading to precipitation of the components constituting the monomer composition. Therefore, the polymerization temperature is preferably 90° C. or lower, or 80° C. or lower.

The water content of the water-containing gel polymer film manufactured through the polymerization step may be about 20% by weight or more, preferably 25% by weight or more, and 40% by weight or less, or 35% by weight or less. Thus, a final superabsorbent polymer film is manufactured by drying the water-containing gel polymer film.

The temperature of the drying step may be preferably in the range of 80° C. to 150° C., or 90° C. to 100° C. When the drying is performed for about 5 minutes to about 30 minutes within the above temperature range, it is possible to obtain the superabsorbent polymer film having the water content of 15% by weight or less, or 12% by weight or less, or 10% by weight or less, or 9% by weight or less, and 1% by weight or more, or 2% by weight or more, or 4% by weight or more, or 6% by weight or more.

The above-described absorbent article of the present disclosure includes the superabsorbent polymer film having a thin thickness and excellent absorbency in the three-dimensional gathers, thereby effectively preventing the body fluid from leaking to the outside without reducing the wearing comfort.

The absorbent article may be a disposable diaper, a sanitary napkin, or an incontinence pad.

Hereinafter, preferred exemplary embodiments will be provided for better understanding of the present invention. However, the following exemplary embodiments are only for illustrating the present invention, and it is apparent to those skilled in the art that various changes and modifications are possible within the scope and spirit of the present invention, and these changes and modifications belong to the scope of the appended claims.

EXAMPLE

Preparation Example: Manufacture of
Superabsorbent Polymer Film

Preparation Example 1

55 g of acrylic acid, 66.6 g of 45 wt % potassium hydroxide (KOH) solution, and 55 g of water were mixed to prepare a neutralization solution, in which 70 mol % of acrylic acid was neutralized.

To the neutralization solution, hydroxyethyl cellulose (HEC, Natrosol 250HR from Ashland, Inc.), glycerin, sodium persulfate as a thermal polymerization initiator, and Irgacure 819 as a photopolymerization initiator were added to prepare a monomer composition having a solid content (TSC) of 54% by weight.

At this time, 0.45 parts by weight of HEC was added, based on 100 parts by weight of the solid content of the monomer composition, 40 parts by weight of glycerin was added, based on 100 parts by weight of acrylic acid, and 1000 ppm of the thermal polymerization initiator and 80 ppm of the photopolymerization initiator were added, based on 100 parts by weight of the monomer composition.

The viscosity at 25° C. of the prepared monomer composition was measured using a TV-22 viscometer manufactured by TOKI, Corp. at spindle #1 and a rotation speed of 1 rpm. As a result, it was confirmed that the viscosity of the monomer composition was 201 mPa·s.

Next, the monomer composition was coated on one surface of a polyethylene terephthalate (PET) film to form a monomer composition film (water content of 12%) with a thickness of 20 μm. A comma coater was used for the coating, and a moving speed of an applicator roll was 0.5 m/min.

Then, the monomer composition film was polymerized by irradiating ultraviolet rays of 370 mJ/cm² to form a water-containing gel polymer film. At this time, the monomer composition film was stretched by applying a tension of 60 N/m in the MD direction while performing polymerization. The thickness of the manufactured water-containing gel polymer film was 20 μm, indicating no significant change, as compared to the monomer composition, and its water content was 12% by weight.

Next, the manufactured water-containing gel polymer film was dried at 80° C. for 5 minutes to manufacture a superabsorbent polymer film (SAP film) having a water content of 9% by weight and a thickness of 19 μm.

Preparation Example 2

A superabsorbent polymer film having a water content of 10% by weight and a thickness of 49 μm was manufactured in the same manner as in Preparation Example 1, except that the thickness of the monomer composition film was 50 μm, the drying temperature of the water-containing gel polymer was 80° C., and the drying time was 10 minutes.

Preparation Example 3

A superabsorbent polymer film having a water content of 11% by weight and a thickness of 189 μm was manufactured in the same manner as in Preparation Example 1, except that the thickness of the monomer composition film was 200 μm, the drying temperature of the water-containing gel polymer was 110° C., and the drying time was 10 minutes.

Examples and Comparative Examples: Manufacture
of Absorbent Article

Comparative Example 1

SAMBO's Fasthann® (basis weight of 186 gsm, a structure in which a complex of superabsorbent polymer (SAP) powder and pulp is wrapped by a tissue, tissue 17%, pulp 62%, SAP 21%) as an absorbent body;

ATPOLY's breathable film (thickness of 17 μm, basis weight of 18 gsm, LLDPE 48%, $CaCO_3$ 48%, $TiO_2$ 2%, other additives) as a liquid-impermeable back sheet; and SAMBO's Softhann® (thickness of 0.34 mm, basis weight of 20 gsm, PE/PP 2de FD 50%, PE/PP 2de SD 50% bicomponent fiber) as a liquid-permeable surface sheet were used.

Toray's hydrophobic SMS (Spunbond+Meltblown+Spunbond) polypropylene nonwoven fabric (thickness of 0.12 mm, basis weight of 12 gsm) to which an elastic member was attached was used as a gather sheet for forming three-dimensional gathers.

The liquid-impermeable back sheet, the absorbent body, and the liquid-permeable surface sheet were sequentially laminated and fixed using a hot press to manufacture a main body portion.

The liquid impermeable back sheet of the main body portion and one end of the gather sheet were combined. Then, the gather sheet was folded back in the width direction and overlapped in two, and then the other end of the gather sheet folded back was fixed to the liquid-permeable surface sheet of the main body portion to manufacture three-dimensional gathers.

Example 1

An absorbent article was manufactured in the same manner as in Comparative Example 1, except that the superabsorbent polymer film (basis weight of 22 $g/m^2$) manufactured in Preparation Example 1 was cut to 2.5 cm*40 cm and interposed between the folded gather sheets during the manufacture of three-dimensional gathers.

Example 2

An absorbent article was manufactured in the same manner as in Comparative Example 1, except that the superabsorbent polymer film having a thickness of 49 μm (basis weight of 51 $g/m^2$) manufactured in Preparation Example 2 was cut to 2.5 cm*40 cm and interposed between the folded gather sheets during the manufacture of three-dimensional gathers.

Example 3

An absorbent article was manufactured in the same manner as in Comparative Example 1, except that the superabsorbent polymer film having a thickness of 189 μm (basis weight of 212 $g/m^2$) manufactured in Preparation Example 3 was cut to 2.5 cm*40 cm and interposed between the folded gather sheets during the manufacture of three-dimensional gathers.

Comparative Example 2

An absorbent article was manufactured in the same manner as in Comparative Example 1, except that an absorbent body including superabsorbent polymer powder and fluff pulp and having a thickness of 2 mm (width*length=2.5 cm*40 cm) was interposed between the folded gather sheets during the manufacture of three-dimensional gathers.

The absorbent body interposed in the three-dimensional gather was manufactured by mixing 40% by weight of fluff pulp having a basis weight of 50 $g/m^2$ and 60% by weight of polyacrylate-based superabsorbent polymer powder having a particle size of 250 to 600 μm (average particle size 400 μm, CRC: 34 g/g, 0.3 psi AUP: 28 g/g) and then wrapping it with a core wrap sheet.

Comparative Example 3

An absorbent article was manufactured in the same manner as in Comparative Example 1, except that the superabsorbent polymer powder fixed with a hot melt adhesive was placed between the folded gather sheets during the manufacture of three-dimensional gathers.

In detail, three-dimensional gathers were manufactured in the following manner. First, on the upper surface of the gather sheet combined with the liquid-impermeable back sheet of the main body portion, a hot melt adhesive (H. B. Fuller, product name: FLC7228AZP) was applied in a size of 2.5 cm*40 cm, and polyacrylate-based superabsorbent polymer powder (average particle size of 400 μm, CRC: 34 g/g, 0.3 psi AUP: 28 g/g) having a particle size of 250 μm to 600 μm was applied thereon at an average thickness of 0.4 mm (that is, the superabsorbent polymer powder was applied as a monolayer, and accordingly, the average particle diameter of the particles becomes the coating thickness). Then, the gather sheet was folded back in the width direction and overlapped in two, and then the other end of the gather sheet folded back was fixed to the liquid-permeable top sheet of the main body portion to manufacture the three-dimensional gather.

Experimental Example

Physical properties of the superabsorbent polymer films of Preparation Examples and the absorbent articles of Examples and Comparative Examples were tested by the following methods, respectively, and the results are shown in Table 1.

Experimental Example 1: Test of Physical Properties of Superabsorbent Polymer Film (1) Water Content (%)

The water content was calculated from the weight of the superabsorbent polymer film specimen before drying (a) and the weight thereof after drying (b). At this time, the drying of the specimen was performed in such a way that the temperature was raised from room temperature (25° C.) to 150° C. for 5 minutes, and then maintained at 150° C. for 15 minutes.

$$\text{Water content (\%)} = (a-b)/a*100$$

(2) Centrifuge Retention Capacity (CRC, g/g)

Centrifuge retention capacity (CRC) was measured according to the EDANA method WSP 241.2. The water contents of the superabsorbent polymer films as measurement objects were as described in Table below, and centrifuge retention capacity was measured without additional adjustment of the water content.

In detail, the superabsorbent polymer film was cut to have the weight (W0) of 0.08 to 0.12 g, and put in a nonwoven fabric bag, followed by sealing. Then, the superabsorbent polymer film was immersed in 0.9% by weight of an aqueous sodium chloride solution (physiological saline) at room temperature. After 30 minutes, the bag was drained off water for 3 minutes using a centrifuge under 250 G, and the weight W2 (g) of the bag was measured. Moreover, after performing the same procedure without using the polymer, the weight W1 (g) at that time was measured. CRC (g/g) was calculated using the respective obtained weights according to the following formula.

$$CRC\ (g/g)=\{[W2(g)-W1(g)]/W0(g)\}-1$$

(3) Tensile Strength (MPa)

The superabsorbent polymer film was cut in a rectangular shape with a size of 20 mm×60 mm and the smooth cutting surface to prepare a specimen. The specimen was installed in a tensile strength analyzer (TAXTplus, Stable Micro Systems) after the initial grip interval was set to 20 mm. The specimen was tensioned at a rate of 0.5 mm per second to measure the force (N) at the time when fracture of the specimen occurred, and the value was divided by the cross-sectional area (mm$^2$) of the specimen to obtain tensile strength (MPa).

(4) Absorbency Under Pressure of 0.7 Psi (AUP, g/g)

Absorbency under pressure (AUP) of 0.7 psi was measured according to the EDANA method WSP 242.2. The water contents of the superabsorbent polymer films of Examples and Comparative Examples as measurement objects were as described in the Table below, and the absorbency under pressure was measured without additional adjustment of the water content.

In detail, a 400 mesh wire net made of stainless steel was mounted on the bottom of a plastic cylinder having an inner diameter of 25 mm. Under conditions of room temperature and humidity of 50%, the absorbent polymer film was cut to have the weight (W3) of about 0.6 g and put on the wire net, and a piston capable of uniformly applying a load of 0.7 psi was put thereon, in which an external diameter of the piston was slightly smaller than 25 mm, there was no gab between the internal wall of the cylinder and the piston, and the jig-jog of the cylinder was not interrupted. At this time, the weight W4 (g) of the apparatus was measured.

After putting a glass filter having a diameter of 90 mm and a thickness of 5 mm in a petri dish having a diameter of 150 mm, a physiological saline solution composed of 0.9% by weight of sodium chloride was poured until the surface level of the physiological saline solution became equal to the upper surface of the glass filter. A sheet of filter paper having a diameter of 90 mm was put on the glass filter. The measurement apparatus was mounted on the filter paper, thereby getting the liquid absorbed under the load for 1 hour. 1 hour later, the weight W5 (g) was measured after lifting the measurement apparatus up.

Absorbency under pressure (g/g) was calculated using the obtained weights according to the following Equation.

$$AUP\ (g/g)=[W5(g)-W4(g)]/W3(g)$$

(5) Elongation (%)

The superabsorbent polymer film was cut in a rectangular shape with a size of 20 mm×60 mm and the smooth cutting surface to prepare a specimen. The specimen was installed in a tensile strength analyzer (TAXTplus, Stable Micro Systems) after the initial gauge length was set to 20 mm. The specimen was tensioned at a rate of 0.5 mm per minutes to measure the gauge length at the time when fracture of the specimen occurred, and the value was divided by the initial gauge length to obtain elongation.

$$Elongation\ (\%)=(L_1-L_0)/L_0*100$$

$L_0$: initial gauge length
$L_1$: gauge length at the point of fracture

TABLE 1

| Absorbent article | Example 1 | Example 2 | Example 3 |
|---|---|---|---|
| SAP film | Preparation Example 1 | Preparation Example 2 | Preparation Example 3 |
| Thickness (μm) | 19 | 49 | 189 |
| Water content (%) | 9 | 10 | 11 |
| CRC (g/g) | 36 | 34 | 35 |
| Tensile strength (MPa) | 11.3 | 14.3 | 27.3 |
| 0.7 psi AUP(g/g) | 13.2 | 11.5 | 9.4 |
| Elongation(%) | 113.2 | 177.1 | 448.3 |

Experimental Example 2: Test of Physical Properties of Absorbent Article (1) Test of Leakage Prevention Function 2 ml of physiological saline (0.9% by weight of an aqueous sodium chloride solution) was injected into the three-dimensional gather of the absorbent article, and it was examined whether the physiological saline leaked out. When leakage occurred, it was evaluated as having no leakage prevention function. When no leakage occurred, it was evaluated as having a leakage prevention function.

As a result, it was confirmed that Comparative Example 1 containing no absorbent material had no leakage prevention function, whereas Examples 1 to 3 and Comparative Examples 2 and 3 showed the leakage prevention function.

However, Comparative Examples 2 and 3 showed that the absorbent articles could not maintain their shape due to the thick three-dimensional gathers, and the sagging of the three-dimensional gathers was observed.

(2) Test of Durability of Three-Dimensional Gather

In order to test durability of the three-dimensional gather when it absorbs physiological saline, the following core integrity test was performed. The absorbent articles of Example 2, Comparative Example 2, and Comparative Example 3 were used for the durability test.

The three-dimensional gather as the test subject was separated from the main body portion, and then used.

80 ml of a 0.9 wt % aqueous sodium chloride solution was allowed to be absorbed into the separated three-dimensional gather, and left for 5 minutes, and then the three-dimensional gather was put on a core integrity testing device capable of providing up and down vibrations, and the test was carried out by applying up and down vibrations 65 times per minute with a falling head of 15 mm. The core integrity testing device was configured with a rod 40 capable of hanging the test subject (three-dimensional gather, 20) and a device (not shown) applying vibration to vibrate the rod up and down, as shown in FIG. 3, and used after being directly manufactured.

At this time, it was visually observed whether the absorbent material (superabsorbent polymer film, superabsorbent polymer powder, or the complex of the superabsorbent polymer powder and fluff pulp) included in the three-dimensional gather was separated, and the number of vibrations at which half of the total amount was separated was examined.

As a result, Comparative Example 2 and Comparative Example 3 showed that half of the superabsorbent polymer powder in the three-dimensional gather was separated, after 120 vibrations and after 40 vibrations, respectively. In contrast, since the three-dimensional gather of Example 2 included the superabsorbent polymer film with excellent flexibility and tensile strength, the superabsorbent polymer film was not separated even after 1000 vibrations or more and exhibited excellent durability.

The above results confirmed that the superabsorbent polymer film has superior durability, as compared to the superabsorbent polymer powder, and thus it is suitably applied to the three-dimensional gather with a lot of movement for the purpose of preventing leakage.

REFERENCE NUMERALS

10: Main body portion
11: Liquid-impermeable back sheet
12: Absorbent body
13: Liquid-permeable top sheet
20, 20a, 20b: Three-dimensional gathers
21: Gather sheet
21a: Proximal end portion of three-dimensional gather
21b: Distal end portion of three-dimensional gather
22: Superabsorbent polymer film
23: Elastic member
30a, 30b: Waist band portions
100: Absorbent article
200: Core integrity testing device

The invention claimed is:

1. An absorbent article comprising:
a main body portion comprising a liquid-impermeable back sheet, an absorbent body comprising a superabsorbent polymer and pulp, and a liquid-permeable top sheet,
wherein the main body portion has a longitudinal direction and a width direction which are perpendicular to each other,
a three-dimensional gather is disposed on each of two sides of the main body portion in the width direction, and extends in the longitudinal direction, the three-dimensional gather comprises a gather sheet, an elastic member, and a superabsorbent polymer film with a thickness of 5 μm to 500 μm,
one end of the gather sheet is bonded with the liquid-impermeable back sheet, and another end thereof is extended outside of the main body portion and folded inward and bonded with the liquid-permeable top sheet,
the superabsorbent polymer film is located in a space between the gather sheet, which is formed by folding the gather sheet, and
one end of the superabsorbent polymer film is located at a bottom of a bonding portion between the liquid-permeable top sheet and the gather sheet.

2. The absorbent article of claim 1, wherein the superabsorbent polymer film has a centrifuge retention capacity of 25 g/g to 50 g/g, as measured according to EDANA method WSP 241.2.

3. The absorbent article of claim 1, wherein the superabsorbent polymer film has a water content of 1% to 15% and a tensile strength of 9 MPa to 50 MPa.

4. The absorbent article of claim 1, wherein the superabsorbent polymer film has elongation of 100% or more, as calculated according to Equation 1:

$$\text{Elongation } (\%) = (L_1 - L_0)/L_0 * 100 \qquad \text{[Equation 1]}$$

wherein in Equation 1,
$L_0$ is an initial gauge length, and
$L_1$ is a gauge length at a point of fracture when a specimen is tensioned at a rate of 0.5 mm per minute.

5. The absorbent article of claim 1, wherein the superabsorbent polymer film has a basis weight of 10 $g/m^2$ to 250 $g/m^2$.

6. The absorbent article of claim 1, wherein the gather sheet has a basis weight of 10 $g/m^2$ to 25 $g/m^2$.

* * * * *